US00PP36678P2

(12) United States Plant Patent
van Haaster et al.

(10) Patent No.: US PP36,678 P2
(45) Date of Patent: May 13, 2025

(54) ***DAHLIA* PLANT NAMED 'DODAHYPNOPREVE'**

(50) Latin Name: *Dahlia variabilis*
Varietal Denomination: DODAHYPNOPREVE

(71) Applicant: DUMMEN GROUP B.V., De Lier (NL)

(72) Inventors: Ans van Haaster, Hillegom (NL); Rami Mousa, De Lier (NL)

(73) Assignee: Dümmen Group B.V., De Lier (NL)

( * ) Notice: Subject to any disclaimer, the term of this patent is extended or adjusted under 35 U.S.C. 154(b) by 5 days.

(21) Appl. No.: 18/665,040

(22) Filed: May 15, 2024

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Dahlia* plant named 'Dodahypnopreve', characterized by its upright and uniformly mounding plant habit; moderately vigorous growth habit; moderate growth rate; freely branching habit; dense and bushy appearance; dark green-colored leaves; freely flowering habit; large double-type inflorescences with dark red-colored ray florets; good postproduction longevity; and good garden performance.

1 Drawing Sheet

Botanical designation: *Dahlia variabilis.*
Cultivar denomination: 'DODAHYPNOPREVE'.

STATEMENT REGARDING PRIOR DISCLOSURES BY INVENTOR AND APPLICANT/ASSIGNEE

A European Community Plant Breeder's Rights application for the instant plant was filed by the Applicant/Assignee, Dümmen Group B.V. of De Lier, The Netherlands on Nov. 15, 2023, application number 2023/2277 with a publication date of Feb. 15, 2024. Foreign priority is claimed to this application.

The Inventors and Applicant/Assignee assert that no sales, offers for sale or public distribution of the instant plant occurred more than one year prior to the effective filing date of this application. Any information about the claimed plant would have been obtained from a direct or indirect disclosure from the Inventors and/or Applicant/Assignee. Inventors and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Dahlia* plant, botanically known as *Dahlia variabilis* and hereinafter referred to by the name 'Dodahypnopreve'.

The new *Dahlia* plant is a product of a planned breeding program conducted by the Inventors in Hillegom and De Lier, The Netherlands. The objective of the breeding program is to create new container *Dahlia* plants that have a freely branching and flowering habit, strong leaves, large attractive inflorescences and good postproduction longevity and garden performance.

The new *Dahlia* plant originated from a cross-pollination conducted by the Inventors during the autumn of 2018 in Hillegom, The Netherlands of two unidentified proprietary selections of *Dahlia variabilis*, not patented. The new *Dahlia* plant was discovered and selected by the Inventors as a single flowering plant from within the progeny of the stated cross-pollination in a controlled greenhouse environment in Hillegom, The Netherlands during the summer of 2019.

Asexual reproduction of the new *Dahlia* plant by vegetative terminal cuttings in a controlled greenhouse environment in De Lier, The Netherlands since the autumn of 2019 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodahypnopreve'. These characteristics in combination distinguish 'Dodahypnopreve' as a new and distinct *Dahlia* plant:

1. Upright and uniformly mounding plant habit.
2. Moderately vigorous growth habit and moderate growth rate.
3. Freely branching habit; dense and bushy appearance.
4. Dark green-colored leaves.
5. Freely flowering habit.
6. Large double-type inflorescences with dark red-colored ray florets.

7. Good postproduction longevity.
8. Good garden performance.

Compared to plants of the parent selections, plants of the new *Dahlia* differ primarily in growth habit as plants of the new *Dahlia* are more uniformly mounded and freely branching than plants of the parent selections.

Plants of the new *Dahlia* can be compared to plants of *Dahlia variabilis* 'Dodahhypelpin', disclosed in U.S. Plant Pat. No. 31,639. In side-by-side comparisons, plants of the new *Dahlia* differ primarily from plants of 'Dodahhypelpin' in the following characteristics:

1. Plants of the new *Dahlia* are taller and stronger than plants of 'Dodahhypelpin'.
2. Plants of the new *Dahlia* are more freely flowering than plants of 'Dodahhypelpin'.
3. Inflorescences of plants of the new *Dahlia* are larger and have larger ray florets than inflorescences of plants of 'Dodahhypelpin'.
4. Ray florets of plants of the new *Dahlia* are dark red in color whereas ray florets of plants of 'Dodahhypelpin' are reddish purple in color.
5. Peduncles of plants of the new *Dahlia* are longer and brown in color whereas peduncles than plants of 'Dodahhypelpin' and shorter and yellow green in color.
6. Plants of the new *Dahlia* have stronger garden performance than plants of 'Dodahhypelpin'.
7. Ray florets of plants of the new *Dahlia* resist fading under high light conditions whereas ray florets of plants of 'Dodahhypelpin' fade under high light conditions.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photograph may differ slightly from the color values cited in the detailed botanical description which accurately describe the colors of the new *Dahlia* plant.

The photograph is a side perspective view of a typical flowering plant of 'Dodahypnopreve' grown in a container.

DETAILED BOTANICAL DESCRIPTION

The aforementioned photograph and the following observations and measurements describe plants grown during the summer in 15-cm containers in a glass-covered greenhouse in De Lier, The Netherlands and under environmental conditions and cultural practices which approximate those generally used in commercial potted *Dahlia* production. During the production of the plants, day temperatures ranged from 18° C. to 30° C., night temperatures ranged from 16° C. to 22° C. and light levels were at least 135 watt/$m^2$. Plants were pinched one time about four weeks after sticking unrooted cuttings. Plants were twelve weeks old when the photograph was taken and eleven weeks old when the description was taken. In the following description, color references are made to The Royal Horticultural Society Colour Chart, Fifth Edition, except where general terms of ordinary dictionary significance are used.

Botanical classification: *Dahlia variabilis* 'Dodahypnopreve'.

Parentage:

*Female, or seed, parent*.—Unidentified proprietary selection of *Dahlia variabilis*, not patented.

*Male, or pollen, parent*.—Unidentified proprietary selection of *Dahlia variabilis*, not patented.

Propagation:

*Type*.—By vegetative terminal cuttings.

*Time to initiate roots, summer*.—About twelve days at temperatures about 22° C. to 30° C.

*Time to initiate roots, winter*.—About 14 days at temperatures about 20° C. to 22° C.

*Time to produce a rooted plant, summer*.—About 21 days at temperatures about 22° C. to 30° C.

*Time to produce a rooted plant, winter*.—About 24 days at temperatures about 20° C. to 22° C.

*Root description*.—Medium in thickness, fibrous; typically whitish grey in color, actual color of the roots is dependent on substrate composition, water quality, fertilizers, substrate temperature and age of roots; tuber development has not been observed on plants of the new *Dahlia*.

*Rooting habit*.—Moderately freely branching; medium density.

Plant description:

*Plant and growth habit*.—Upright and uniformly mounding plant form; overall shape, globose; freely basal branching habit with about four primary lateral branches per plant and each primary lateral branch with about four to five secondary lateral branches; dense and bushy appearance; pinching is not required, but will enhance lateral branch development; inflorescences held above the foliar plane on moderately strong peduncles; moderately vigorous growth habit and moderate growth rate.

*Plant height, soil level to top of foliar plane*.—About 22 cm.

*Plant height, soil level to top of floral plane*.—About 30 cm to 35 cm.

*Plant diameter or spread*.—About 30 cm to 35 cm.

*Lateral branches*.—Length: About 20 cm. Diameter: About 9 mm. Internode length: About 2 cm to 3 cm. Aspect: Mostly upright. Strength: Moderately strong. Texture and luster: Smooth, glabrous; semi-glossy. Color, developing and developed: Close to 144A.

Leaf description:

*Arrangement*.—Opposite; leaves may be single or compound with typically three to five leaflets.

*Leaf length*.—About 8 cm to 22 cm.

*Leaf width*.—About 10 cm to 17 cm.

*Leaflet length*.—About 8 cm to 10 cm.

*Leaflet width*.—About 5.5 cm.

*Leaf and leaflet shape*.—Ovate.

*Leaf and leaflet apex*.—Acute.

*Leaf and leaflet base*.—Attenuate.

*Leaf and leaflet margin*.—Dentate; indentations are shallow and divergent.

*Leaf and leaflet venation pattern*.—Pinnate.

*Leaf and leaflet texture and luster, upper surface*.—Smooth, glabrous; semi-glossy.

*Leaf and leaflet texture and luster, lower surface*.—Smooth, glabrous; matte.

*Color*.—Developing leaves and leaflets, upper and lower surfaces: Close to 137A. Fully expanded leaves and leaflets, upper surface: Close to 137A; venation, close to 144A. Fully expanded leaves and leaflets, lower surface: Close to 138B; venation, close to 143C.

*Petioles*.—Length: About 5.5 cm. Diameter: About 4 mm. Strength: Moderately strong. Texture and luster, upper and lower surfaces: Smooth, glabrous; semi-glossy. Color, upper and lower surfaces: Close to 144A.

Inflorescence description:

*Appearance and arrangement*.—Double-type inflorescence form with ray florets forming acropetally on a receptacle; inflorescences positioned above the foliar plane on moderately strong peduncles; inflorescences face mostly upright to slightly outwardly; freely flowering habit with about 14 developing and fully developed inflorescences per plant at one time.

*Fragrance*.—None detected.

*Time to flower*.—Early flowering habit, plants begin flowering about ten to twelve weeks after planting; in the garden in The Netherlands, plants flower continuously from spring until late summer.

*Post-production longevity*.—Depending on temperatures, inflorescences maintain good substance for about two to three weeks on the plant; inflorescences persistent.

*Inflorescence buds*.—Height: About 1.5 cm. Diameter: About 1.5 cm. Shape: Globular. Texture and luster: Smooth, glabrous; glossy. Color: Close to 144B.

*Inflorescence size*.—Diameter: Large, about 12.5 cm. Depth (height): About 3 cm to 3.5 cm. Disc diameter: About 1.2 cm. Receptacle height: About 2 mm to 3 mm. Receptacle diameter: About 1.5 cm. Receptacle color: Close to 144A.

*Ray florets*.—Quantity per inflorescence: About 100 to 120 arranged in about eleven whorls. Length: About 5.5 cm. Width: About 2.2 cm. Shape: Oblong. Apex: Retuse. Base: Attenuate. Margin: Entire; moderately undulate. Aspect: Initially upright and with development, outwardly. Texture and luster, upper and lower surfaces: Smooth, glabrous; matte. Color: When opening, upper surface: Close to 46B. When opening, lower surface: Close to 45A. Fully opened, upper surface: Close to 46B; venation, close to 46A; color does not change with subsequent development. Fully opened, lower surface: Close to 45A; venation, close to 46A; color does not change with subsequent development.

*Disc florets*.—Quantity per inflorescence: About 40 to 60. Length: About 8 mm. Diameter: About 1 mm. Shape: Tubular, elongated; apices retuse. Texture and luster: Smooth, glabrous; glossy. Color, fully opened, inner and outer surfaces: Close to 17B.

*Phyllaries*.—Quantity per inflorescence: About seven arranged in a single whorl. Length: About 2 cm. Width: About 5 mm to 8 mm. Shape: Ovate. Apex: Acute. Base: Attenuate. Margin: Entire. Texture and luster, upper and lower surfaces: Smooth, glabrous; semi-glossy. Color, upper surface: Close to 137A. Color, lower surface: Close to 137B.

*Peduncles*.—Length, terminal peduncle: About 8 cm. Diameter, terminal peduncle: About 3 mm. Aspect: Mostly erect to slightly outwardly. Strength: Moderately strong. Texture and luster: Smooth, glabrous; semi-glossy. Color: Close to 165A.

*Reproductive organs*.—Androecium: Present on disc florets only. Stamen quantity per floret: Five to six. Filament length: About 9 mm. Filament color: Close to 13A. Anther length: About 4 mm. Anther color: Close to 17A. Pollen amount: Moderate. Pollen color: Close to 17A. Gynoecium: Present on disc florets only. Pistil quantity per floret: One. Pistil length: About 1 cm. Style length: About 5 mm. Style color: Close to 144D. Stigma diameter: Less than 1 mm. Stigma shape: Bifurcate. Stigma color: Close to 17B. Ovary color: Close to 145C. Seeds: To date, seed development has not been observed on plants of the new *Dahlia*.

Pathogen & pest resistance: To date, plants of the new *Dahlia* have not been observed to be resistant to pathogens and pests common to *Dahlia* plants.

Temperature tolerance & garden performance: Plants of the new *Dahlia* tolerate high temperatures about 35° C. and low temperatures about 10° C. Plants of the new *Dahlia* have been observed to have good garden performance and to resist fading of the ray floret color under high light conditions.

It is claimed:

1. A new and distinct *Dahlia* plant named 'Dodahypnopreve' as illustrated and described herein.

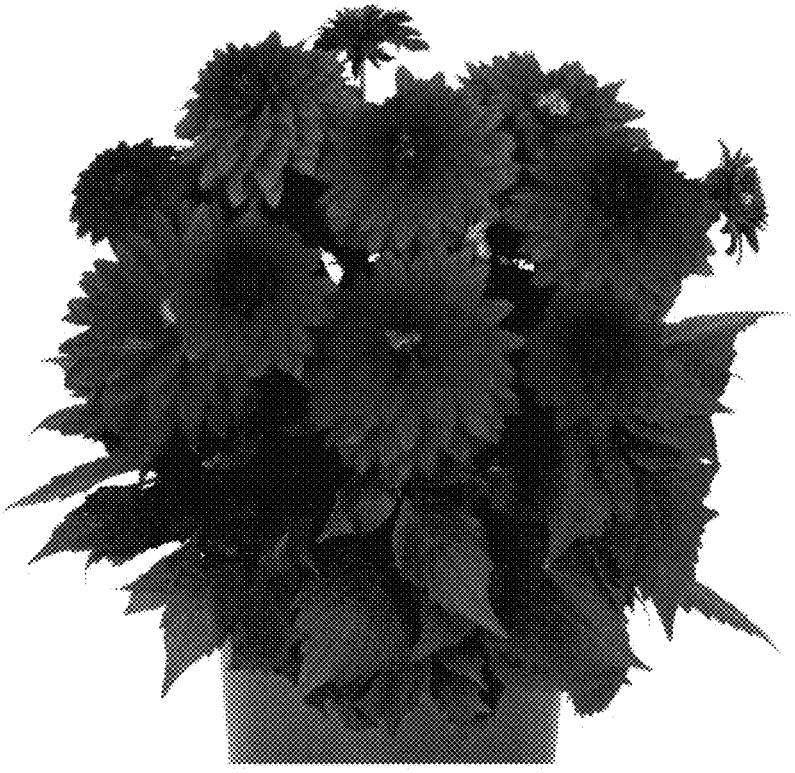

* * * * *